(12) United States Patent
Rudischhauser et al.

(10) Patent No.: US 6,419,628 B1
(45) Date of Patent: Jul. 16, 2002

(54) ENDOSCOPE WITH LONGITUDINAL COMPENSATION CAPABILITY IN RESPONSE TO THERMAL STRESS

(75) Inventors: Jürgen Rudischhauser, Tuttlingen; Klaus Renner, Liptingen; Siegfried Höfig, Tuttlingen, all of (DE)

(73) Assignee: Karl Storz GmbH & Co. KG (DE)

(*) Notice: Subject to any disclaimer, the term of this patent is extended or adjusted under 35 U.S.C. 154(b) by 0 days.

(21) Appl. No.: 09/407,680

(22) Filed: Sep. 28, 1999

Related U.S. Application Data

(63) Continuation of application No. PCT/EP98/01826, filed on Mar. 27, 1998.

(30) Foreign Application Priority Data

Mar. 29, 1997 (DE) .......................................... 197 13 275

(51) Int. Cl.[7] .................................................. A61B 1/00
(52) U.S. Cl. ........................ 600/161; 600/133; 600/130
(58) Field of Search ................................ 600/161, 172, 600/138, 136, 130, 133

(56) References Cited

U.S. PATENT DOCUMENTS

| 4,063,796 A | * | 12/1977 | Hiltebrandt | ................. | 600/161 |
|---|---|---|---|---|---|
| 4,776,668 A | * | 10/1988 | Fujimoto | .................... | 600/161 |
| 4,779,613 A |   | 10/1988 | Hashiguichi et al. | .......... | 128/6 |
| 4,813,400 A | * | 3/1989  | Washizuka et al. | .......... | 600/161 |
| 5,199,417 A | * | 4/1993  | Muller et al. | ................ | 600/138 |
| 5,443,057 A | * | 8/1995  | Elmore | ......................... | 600/133 |
| 5,601,525 A | * | 2/1997  | Okada | ......................... | 600/160 |
| 5,706,143 A |   | 1/1998  | Hipp | ........................... | 359/824 |

FOREIGN PATENT DOCUMENTS

| DE | 3708124 A1 | 9/1987 |
| DE | 3735771 A1 | 5/1988 |
| DE | 3707787 A1 | 9/1988 |
| DE | 19521654 A1 | 12/1996 |
| DE | 19713275 A1 | 10/1998 |
| WO | WO96/05764 | 2/1996 |

\* cited by examiner

*Primary Examiner*—John P. Leubecker
(74) *Attorney, Agent, or Firm*—St. Onge Steward Johnston & Reens LLC

(57) ABSTRACT

An endoscope has an outer tube that is joined to an optical head having an observation element at its end, which elements are sealingly fitted forming a first module element. An inner tube sealingly fitted together with a housing containing optical elements form a second module element having the optical components hermetically closed. The second module element is disposed in the first module element having its distal ends rigidly and sealingly fitted together. The housing of the second module elements extends into said optical head of that first module element and is supported therein allowing relative movement between housing and optical head when thermally stressed.

12 Claims, 3 Drawing Sheets

ENDOSCOPE WITH LONGITUDINAL COMPENSATION CAPABILITY IN RESPONSE TO THERMAL STRESS

CROSSREFERENCE OF PENDING APPLICATION

This application is a continuation of pending international application PCT/EP 98/01826 filed on Mar. 27, 1998.

BACKGROUND OF THE INVENTION

1. Field of the Invention

The present invention relates to an endoscope, having an outer tube that is joined to an optical head that carries an eyepiece cup or an adapter device for a camera system or an integrated miniature camera, also having an inner tube, arranged in the outer tube and extending into the optical head and supported there, that carries optical components, the outer tube and inner tube being rigidly and sealingly joined to one another at the distal end of the endoscope.

2. Related Prior Art

Endoscopes of this kind are commonly known, and are marketed in this configuration, for example, by the Applicant.

Optical components, for example rod lenses, are arranged in the inner tube; further components extend into the optical head. It is possible to observe through the optical system from the proximal end of the eyepiece cup, which has a window. In other embodiments, instead of the eyepiece cup an adapter device for a camera is provided, or a miniature camera is directly integrated. These three embodiments represent an observation element of the optical head. The outer tube, which surrounds the inner tube, delimits an annular space around the outer side of the inner tube that serves to guide light guides, for example glass fibers, to the distal end of the endoscope in order to illuminate the point being observed. The glass fibers are usually conveyed into this annular space via a radially protruding fitting on the optical head. At the distal end, the outer tube and inner tube are immovably joined to one another via a sealed join, so that no liquids or gases can penetrate into the interior of the endoscope from that end.

After operations have been performed the endoscopes must be sterilized, for which purpose they are heated in autoclaves to temperatures in the range from 130 to 140° C.

Now that minimally invasive procedures have become routine and, for example in hospitals, numerous endoscopically observed operations are performed every day, the endoscopes are in frequent use and are consequently subjected to severe mechanical stresses, especially during autoclaving. In order for endoscopes to be available again as quickly as possible after operations, so-called "flash autoclaves" have been developed, in which all of the endoscopes are heated to 143° C. and then quenched with cold water. These extreme temperature changes must be handled from a mechanical standpoint so that thermal expansion does not cause any damage to the optical system, for example causing it to leak and allowing moisture to penetrate into the optical system. An expansion compensation capability must therefore be created for such temperature shocks. This compensation capability is substantially a longitudinal expansion compensation capability for the elongated endoscopes.

In one known solution, the proximal end of the outer tube is mounted in axially movable fashion in the optical head, and a corresponding O-ring provides sealing closure. This creates a longitudinal expansion compensation capability in response to the aforementioned temperature shocks.

A disadvantage of this design is that because of the movable mounting arrangement, the mechanical stability of the join between outer tube and optical head cannot be guaranteed for the long term. A torque acts on the joining point when an endoscope is set down, since the optical head usually has a greater diameter than the outer tube and transitions via a step into the slender endoscope shaft. If this join between the outer tube and optical head loosens, not only is mechanical stability impaired, but there is also the possibility that moisture may penetrate into the interior of the optical head and damage the optical system.

In a further known design as disclosed by the company styled Richard Wolf GmbH, Germany, the proximal end of the inner tube is supported sealingly via an O-ring, but in axially movable fashion, on the inner side of the optical head. If this sealing point becomes leaky as a result of numerous longitudinal expansions during autoclaving cycles, there exists the risk that moisture may penetrate directly into the inner tube and thus into the optics.

It is therefore the object of the present invention to provide an endoscope remaining mechanically stable over a long term, in particular even after numerous flash autoclaving cycles, and having longitudinal expansion capability, without the possibility for contaminants to penetrate into the optical components.

SUMMARY OF THE INVENTION

According to the present invention, the object is achieved in that outer tube, optical head, and observation element are fitted together to form an immovable first module that is sealed among these parts but not closed off from the outside; and that at its proximal end the inner tube is immovably and sealingly fitted together with a housing that hermetically closes off the optical components, to form a second module.

Because the outer components, namely the outer tube, optical head, and observation elements (eyepiece cup, or adapter, or integrated miniature camera) are fitted together into a fixed module, mechanical effects—whether due to mechanical impacts when the unit is set down, or handling, or expansion effects in response to thermal shock—cannot result in any relative displacements of the components in this rigid assemblage. The latter possesses long-term dimensional stability, and the individual components—outer tube, optical head, and eyepiece cup—remain immovably and nondisplaceably fitted to one another. The fact that fitting is accomplished in such a way that these parts are fitted sealedly together with one another creates a module into which moisture, gases, or other contaminants cannot enter from the outside, with the exception of the two openings on the ends.

Because of the fact that at its proximal end, the inner tube is immovably and sealingly fitted together with a housing that hermetically closes off the optical components, forming a second module, the optical elements are hermetically sealed off from the outside world, so that no contaminants, whether gaseous or liquid, can penetrate into the optical system.

These two modules are rigidly and sealedly joined to one another at the distal end. At the proximal end, the inner tube and the proximal end of the hermetically sealing housing are then supported in the optical head. The longitudinal expansions or shrinkages of the two elongated modules that occur in response to temperature shocks can now take place in undisturbed fashion alongside one another, proceeding from the fixed distal linkage point between these two modules. Unequal longitudinal expansions of the modules can now be permitted by way of relative movements between them. This relative movement on the one hand does not result in any impairment of the mechanical stability of the endoscope, since the latter is substantially secured by the external enveloping assemblage of the first module made up of the outer tube, optical head, and eyepiece cup. This relative movement also cannot result in leaks in the optical system, since the inner second module is hermetically sealed within itself. In the optical head, sealing measures are taken in a manner known per se, for example by way of O-rings, between the outer side of the inner second module and the inner side of the outer first module, so that water or steam cannot penetrate during autoclaving. If this should nevertheless happen, it is not detrimental to mechanical stability nor does it have any negative influence on the optical system, since the latter is, as such, hermetically sealed.

In an embodiment of the invention, the proximal end region of the second module is supported in floating fashion in the optical head.

The advantage of this feature is that this floating mounting system, which is nevertheless sealed in terms of the penetration of autoclaving steam or liquid, allows jam-free longitudinal expansion in response to temperature shocks and also makes it possible for radially acting mechanical shocks or impacts, when an endoscope is set down or inadvertently dropped, to be absorbed or distributed in such a way that no damage occurs to the optical system. The optical system contains numerous lenses, for example relatively long rod lenses made of glass materials, that could possibly break in the event of intense mechanical shocks. The floating mounting system allows such shocks to be absorbed more gently or in more damped fashion, thereby considerably extending the life span of the lens system.

In a further embodiment of the invention, the proximal end region of the second module is supported in stationary fashion on the optical head and is equipped with expansion features.

In contrast to the embodiment described previously, in which the inner second module can displace in the proximal direction, this capability does not exist here because of the stop, and the longitudinal compensation capability is provided by way of the expansion features. In this case the proximal end of the inner module can be permanently held at a very specific point; this end is usually closed off with a glass window or lenses in order to ensure visibility through the inner tube. Readjustments of the optics due to relative motion are no longer necessary. The necessary longitudinal expansion is brought about via the expansion features.

In a particularly preferred embodiment of this design, the expansion feature consists in a bellows-like configuration of the wall of the housing.

The bellows absorbs the requisite changes in shape when expansion or shrinkage events occur, so that the other components, especially the lenses, remain in an unchangeable position relative to one another.

In a further embodiment of the invention, both the immovable sealed join among the individual components of the two modules and the join between the modules at the distal end are accomplished by soldering, welding, or adhesive bonding.

The advantage of this feature is that with the use of common working methods it is possible to create not only the corresponding mechanical bond between the parts that are to be joined, but also the correspondingly sealed join that withstands, over the long term, both mechanical shocks and temperature shocks.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

The invention will be described and explained in more detail below with reference to several selected exemplary embodiments in conjunction with the appended drawings, in which.

DETAILED DESCRIPTION OF PREFERRED EMBODIMENTS

Figure 1:
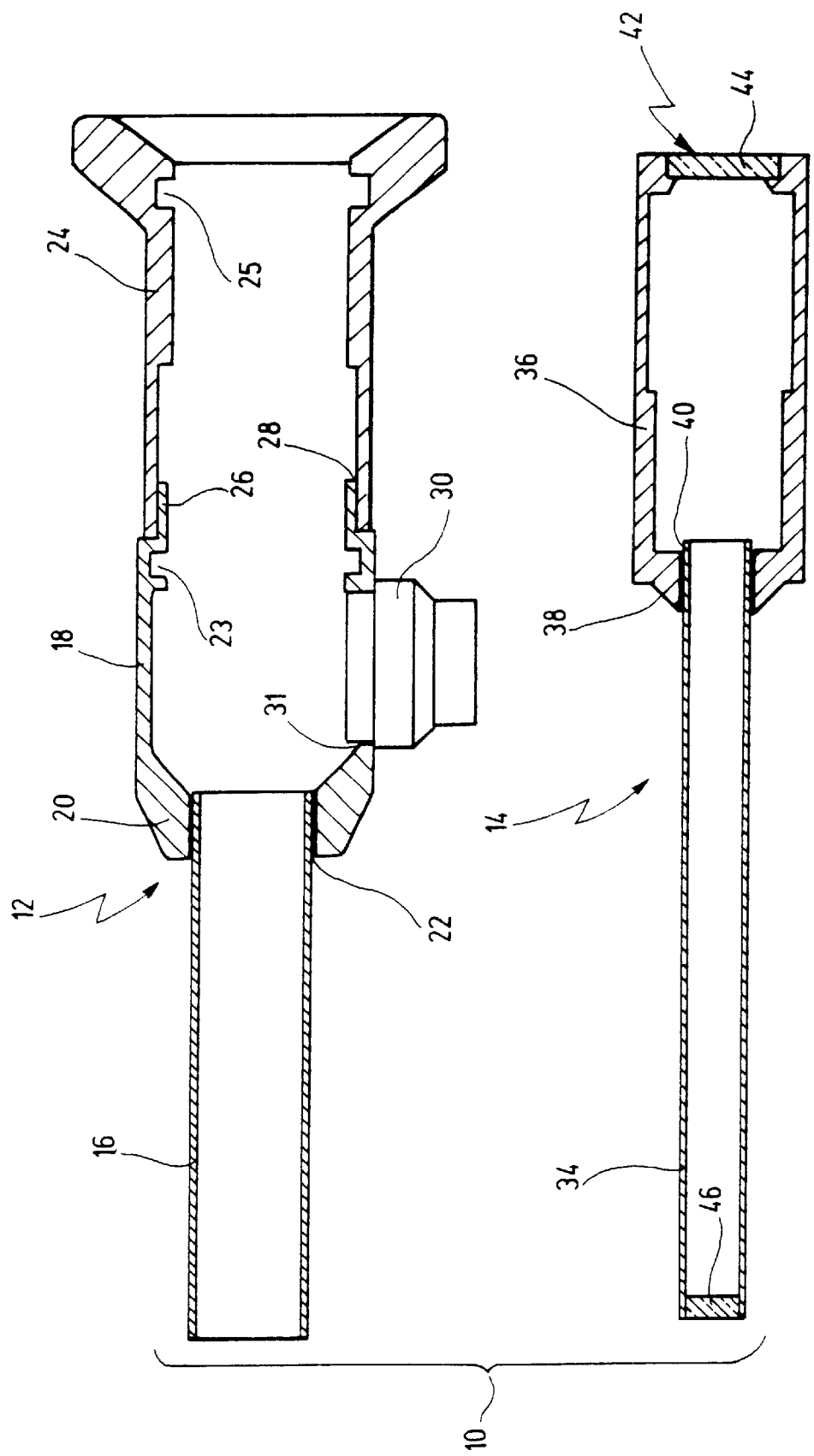
FIG. 1 shows a longitudinal section through the two modules of an endoscope according to the present invention, in the separated state when not yet joined to one another, the optical components being omitted for the sake of clarity.
Figure 2:
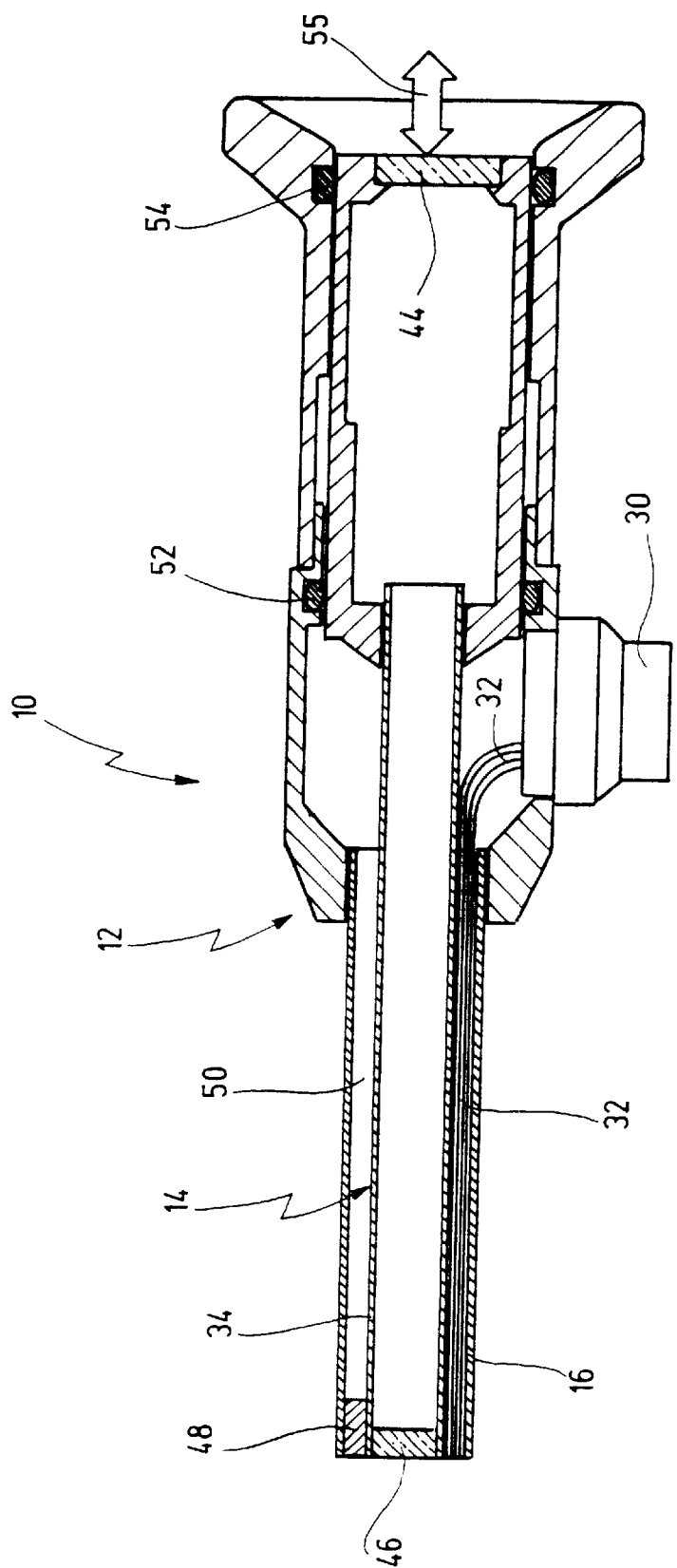
FIG. 2 shows the assemblage of the two modules of FIG. 1, the optical components (such as lenses) once again being omitted for reasons of clarity.

An endoscope shown in FIGS. 1 and 2 is labeled in its entirety with the reference number 10.

Endoscope 10 substantially comprises a first module 12 and a second module 14, as shown in FIG. 1 lying separately one below the other.

First module 12 has an outer tube 16 whose length varies depending on the purpose of the endoscope and which is shown in the representation as a relatively short outer tube 16.

Outer tube 16 is joined at the proximal end to a optical head 18.

Optical head 18 has an approximately hollow cylindrical housing at whose distal end an installation flange 20 is provided.

The proximal end of outer tube 16 is inserted into flange 20, and a mechanically stable and absolute gas- and water-tight join 22 is created between these components by soldering.

Optical head 18 is joined at the proximal end to an eyepiece cup 24.

Projecting proximally for this purpose is a tubular flange 26 onto which eyepiece cup 24 is slid. Join 28 in this region is accomplished by thread-joining and adhesive bonding.

A radially protruding fitting 30, which is also adhesively bonded by way of a gas- and liquid-tight join 31, is mounted on optical head 18.

An annular groove 23 is configured on the inner side of optical head 18 in the region of tubular flange 26; a corresponding annular groove 25 is configured in the region of the proximal end of the eyepiece cup.

This configuration results in a mechanically very stiff and resistant structure in the form of first module 12.

Second module 14 comprises an inner tube 34 that is equipped at the proximal end with a housing 36. Housing 36 has at the distal end a flange 38 into which the proximal end of inner tube 34 is inserted. A gas- and liquid-tight join 40 is produced by soldering these two elements to one another. Housing 36 is hollow and cylindrical. At the distal end, inner tube 34 is closed off by a transparent disk 46 that is soldered in. The proximal end of housing 36 is equipped with a disk 44 that is also soldered in in gas- and liquid-tight fashion, as is also the case with disk 46.

Disks 44 and 46 constitute the end boundaries of an optical system, received in the interior of housing 36 and of inner tube 34, that is not further shown here for reasons of clarity. Assembling second module 14 in the manner described earlier results in a hermetically sealed structure in which the entire optical system is received in a manner protected against the penetration of contaminants.

During assembly, second module 14 is inserted from the proximal end into first module 12 until the distal ends of outer tube 16 and inner tube 34 come to rest at approximately the same level.

As is evident from FIG. 2, they are joined to one another in mechanically immovable and sealing fashion in the distal region via a join 48. Join 48 can, for example, comprise a ring that is soldered to the outer side of inner tube 34 and to the inner side of outer tube 16. An annular space 50 is now created between inner tube 34 and outer tube 16, into which, for example, optical fibers 32 are guided to the distal end through fitting 30. Join 48 then provides corresponding light outlet openings.

O-ring seals 52 and 54, which create a sealed closure between the outer side of housing 36 and the inner side of optical head 18 or eyepiece cup 24, are placed into annular grooves 23 and 25, respectively.

The outside diameter of housing 36 is slightly smaller than the inside diameter of optical head 18 and eyepiece cup 24.

This ensures floating support and mounting of housing 36, allowing longitudinal expansion in response to temperature changes, as indicated in FIG. 2 by double arrow 55. Upon expansion, the proximal end of housing 36 of inner second module 14 thus shifts proximally toward the end of eyepiece cup 24.

O-ring seals 52 and 54 allow these movements and also, to some extent, absorb radially applied mechanical impacts.

Figure 3:
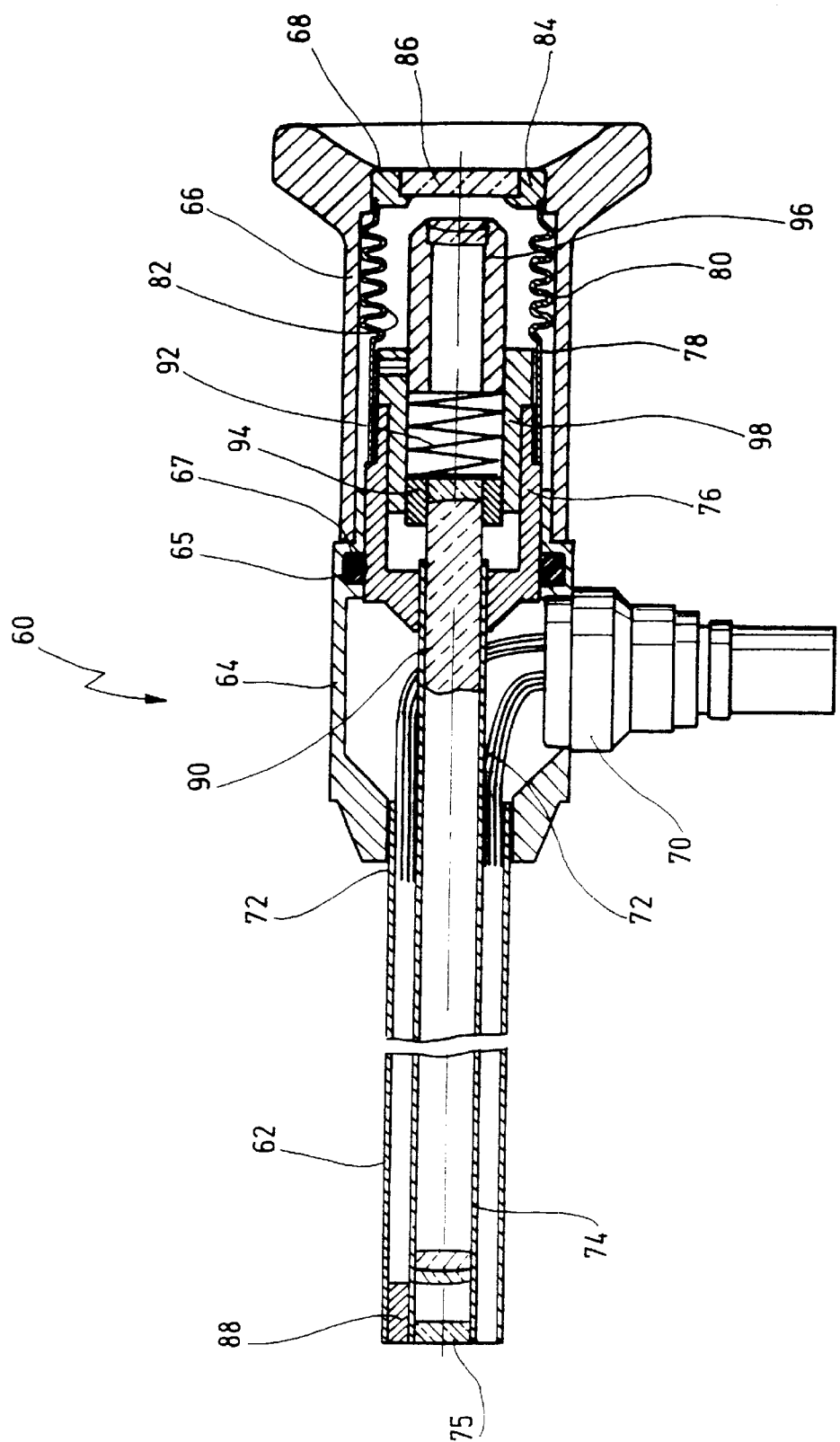
FIG. 3 shows a sectioned representation, comparable to the sectioned representation of FIG. 2, of a further exemplary embodiment including the optical components.

In a further exemplary embodiment of an endoscope 60 according to the present invention shown in FIG. 3, a first outer module is again present, made up of an outer tube 62, an optical head 64, and an eyepiece cup 66 that again are fitted to one another as described earlier. A radially projecting fitting 70 serves in similar fashion to convey optical fibers 72.

A corresponding annular groove 65 is provided in this case at the point where annular groove 23, described earlier in conjunction with FIG. 1, is configured.

A stop 68, whose purpose will be explained later, is provided at the proximal end of eyepiece cup 66.

The inner second module is again composed of an inner tube 74 and a housing 76. The inner tube is once again closed off distally by a disk 75.

In contrast to the exemplary embodiment shown in conjunction with FIGS. 1 and 2, a proximal segment 78 of housing 76 is configured as a relatively thin wall 80 that assumes the shape of a bellows 82. The proximal end of corrugated bellows 82 is immovably soldered to a ring that carries at its center a disk 86.

Ring 84 sits on stop 68, and the proximal end of the inner second module is thereby immobilized.

As described above, the distal end of inner tube 74 is joined by a join 88 to the distal end of outer tube 62.

The necessary longitudinal expansion is now absorbed by the deformation of bellows 82.

It is evident from the sectioned representation in FIG. 3 that numerous rod lenses 90, which are held pressed together by way of a helical spring 92, are received in inner tube 74. For this purpose, spring 92 pushes a cap 94 onto the assemblage of rod lenses 90. At the opposite end, spring 92 braces against a tubular extension 96 that is immovably joined to an intermediate housing 98 that surrounds spring 92.

This arrangement, known per se, allows a slight relative movement among rod lenses 90, so that abrasion points are not created. The pressure of spring 92, however, holds rod lenses 90 against one another.

An O-ring seal 67 is received in annular groove 65 so that the assemblage of inner tube 74 and housing 76 is supported in approximately floating fashion in this region, and only at the proximal end sits immovably on stop 68.

This design allows for longitudinal expansion and shrinkage in response to temperature shocks, while the relative positions of the optical system lenses are maintained.

Both O-ring seal 67 and corrugated bellows 82 make it possible for mechanical impacts or thermal shocks to be absorbed and distributed to this extent without exposing rod lenses 90, which are made of glass materials, to a risk of breakage.

If any adjustment or relative displaceability of the lens system should nevertheless be desired, whether for focusing or for adjustment, this can be accomplished by way of noncontact couplings, for example magnetic couplings.

For example, an inner magnetic ring that is in nonpositive rotary connection with an outer magnet ring applied over the outer side of eyepiece cup 66 can be provided in the region of tubular extension 96. In this case threads are then provided to convert a rotary movement of the inner magnetic ring into an axial displacement of tubular extension 96. This displacement capability can be implemented without modifying the design principle of the two modules.

What is claimed is:

1. An endoscope comprising
   an outer tube that is joined to an optical head provided at its end opposite to said outer tube with an observation element, said outer tube, said optical head and said observation element are sealingly fitted together to form a first module element having an opening,
   an inner tube sealingly fitted to a housing containing optical components, said inner tube and said housing hermetically closes said optical elements thereby forming a second module element, said second module element is inserted via said opening into said first module element, wit a distal end of said outer tube rigidly and sealingly joined to a distal end of said inner tube, wherein
      said housing of said inner tube extends into said optical head, and said housing is supported by said optical head in a manner allowing relative movements between housing and optical head when thermally stressed, and wherein
      a proximal end portion of said second module is supported in a stationary fashion in said optical head and is equipped with expansion means.

2. The endoscope of claim 1, wherein said expansion means comprise a bellows-like configuration of a wall of said housing of said second module element.

3. The endoscope of claim 1, wherein said outer tube, optical head and observation element are soldered.

4. The endoscope of claim 1, wherein said outer tube, optical head and observation element are welded.

5. The endoscope of claim 1, wherein said outer tube, optical head and observation element are adhesively bonded.

6. The endoscope of claim 1, wherein said observation element is selected from the group consisting of an eye piece cup, an adapter device for a camera system, and an integrated miniature camera.

7. The endoscope of claim 1, wherein said inner tube and housing are soldered.

8. The endoscope of claim 1, wherein said inner tube and housing are welded.

9. The endoscope of claim 1, wherein said inner tube and housing are adhesively bonded.

10. The endoscope of claim 1, wherein said first module and second module are soldered.

11. The endoscope of claim 1, wherein said first module and second module are welded.

12. The endoscope of claim 1, wherein said first module and said second module are adhesively bonded.

* * * * *